(12) United States Patent
Langston et al.

(10) Patent No.: US 7,164,025 B2
(45) Date of Patent: Jan. 16, 2007

(54) MANUFACTURE OF SINGLE ISOMER METHYLPHENIDATE

(75) Inventors: Marianne Langston, Cambridge (GB); Hooshang Shahriari Zavareh, Cambridge (GB)

(73) Assignee: Celltech Pharma Europe Limited (GB)

( * ) Notice: Subject to any disclaimer, the term of this patent is extended or adjusted under 35 U.S.C. 154(b) by 446 days.

(21) Appl. No.: 09/928,139

(22) Filed: Aug. 10, 2001

(65) Prior Publication Data

US 2002/0032335 A1 Mar. 14, 2002

Related U.S. Application Data

(63) Continuation of application No. 08/792,415, filed on Feb. 3, 1997.

(60) Provisional application No. 60/021,135, filed on Sep. 12, 1996.

(30) Foreign Application Priority Data

Feb. 2, 1996 (GB) ................................. 9602174.6
Sep. 10, 1996 (GB) ................................. 9618836.2

(51) Int. Cl.
*C07D 211/34* (2006.01)
(52) U.S. Cl. ..................................... 546/240; 546/203
(58) Field of Classification Search ............... 546/203, 546/240
See application file for complete search history.

(56) References Cited

U.S. PATENT DOCUMENTS

| | | | | |
|---|---|---|---|---|
| 2,957,880 A | * | 10/1960 | Rometsch | 546/240 |
| 4,254,261 A | * | 3/1981 | Miller | 546/203 |
| 5,733,756 A | * | 3/1998 | Zeitlin et al. | 435/122 |
| 6,121,453 A | * | 9/2000 | Zavareh | 546/238 |
| 6,242,464 B1 | * | 6/2001 | Harris | 514/317 |

FOREIGN PATENT DOCUMENTS

WO   WO 97/27176   * 7/1997

OTHER PUBLICATIONS

Miller et al. "Racemization of . . . " CA 94:47148 (1980).*
Barry "Racemization of alpha-amino acid ester . . . " CA 119:73084 (1993).*
Jacques et al. "Enantiomers, Racemates . . . " Krieger, p. 259-261 (1981).*
Shaflee et al. "The absolute confuguration of the epneyiramines . . . " J. Med. Chem. v. 12, p. 266-270 (1969).*
Armstrong et al. "separation of drug . . . " Science v. 232, p. 1132-1135 (1986).*
Branko et al. "Determination of enantiomeric . . . " Tetrahedron Assym. vo. 5, p. 1711-1716 (1994).*
Barry et al. "Racemization . . . " CA 119:73084 (1993).*
Miller "Racemization . . . " CA 94:47148 (1981).*
Frigeriio et al. "Sensitive procedure . . . " CA 120:235242 (1994).*
Yakhotov et al. "Threo and erythro . . . " CA 81:41337 (1974).*
Kratchanov et al. "Chromatographic resolution . . . " CA 70:28781 (1969).*
Beausoleil et al. "5-ter-butylproline" J. Org. Chem. 61 p. 9447-9454 (1996).*
Gao et al. "Synthesis and separation of optically active compounds" Ann. Phar. Fran. v. 52, p. 184-203 (1994).*
Shimoju et al. "Preparation of DL erythro or DL threo phenylserine derivative" CA 114:123080 (1991).*
Patrick, K. et al. "Pharmacology of the Enantiomers of *threo*-Methylphenidate" *The Journal of Pharmacology and Experimental Therapeutics*, Jan. 8, 1987, pp. 152-158, 241(1).

* cited by examiner

*Primary Examiner*—Celia Chang
(74) *Attorney, Agent, or Firm*—Saliwanchik, Lloyd & Saliwanchik

(57) ABSTRACT

The present invention pertains to a process for obtaining a single enantiomer, d or l, of threo-methylphenidate, comprising resolution of a mixture of the enantiomers; racemisation of the unwanted enantiomer, to give a mixture of all four stereoisomers; and separation of the erythro stereoisomers, to leave the same mixture of enantiomers for resolution.

8 Claims, No Drawings

MANUFACTURE OF SINGLE ISOMER METHYLPHENIDATE

CROSS-REFERENCE TO RELATED APPLICATIONS

This application is a continuation of U.S. application Ser. No. 08/792,415, filed Feb. 3, 1997, which claims priority from U.S. Provisional Application Ser. No. 60/021,135, filed Sep. 12, 1996, now abandoned.

FIELD OF THE INVENTION

This invention relates to an economic process for the manufacture of a single isomer of methylphenidate.

BACKGROUND OF THE INVENTION

Methylphenidate was first prepared as a mixture of the erythro [R*S*] and threo [R*R*] racemates. U.S. Pat. No. 2,957,880 discloses studies upon the two racemic mixtures, which revealed that the therapeutic activity resides in the threo diastereoisomer. It is now considered that it is the d-threo [or (R,R)] enantiomer that has the preferred therapeutic activity. Uses of this enantiomer are disclosed in PCT/GB96/01688 (International Publication No. WO 97/03671), PCT/GB96/01689 (International Publication No. WO 97/03672) and PCT/GB96/01690 (International Publication No. WO 97/03673), the contents of which are incorporated herein by reference.

The resolution of threo-methylphenidate can be achieved using the expensive resolving agent 1,1'-binaphthyl-2,2'-diyl hydrogen phosphate, a process first reported by Patrick et al, The Journal of Pharmacology and Experimental Therapeutics, 241:152–158 (1987). A more efficient resolution, using a O,O'-diaroyltartaric acid, is disclosed in PCT/GE97/00185, the contents of which are incorporated by reference: in particular, the use of O,O'-di-p-toluoyltartaric acid allows the diastereoisomeric salts to be very readily separated.

In an alternative approach, disclosed in U.S. Pat. No. 2,957,880, the amide of erythro-methylphenidate (i.e. as -CONH$_2$ instead of -CO$_2$Me) is resolved using tartaric acid. However, this resolution must be followed by amide hydrolysis, and equilibration at the benzylic centre, to give the threo isomer of the carboxylic acid (ritalinic acid) which is esterified. U.S. Pat. No. 2,957,880 describes a general process for conversion of erythro diastereoisomers to threo diastereoisomers, using alkali and elevated temperature.

In order to establish an economic resolution process, it is highly desirable to be able to recycle the unwanted enantiomer into the resolution by way of a racemisation. This becomes especially important when the resolution is performed late in a synthesis. An example of such a resolution and racemisation procedure is in the case of naproxen where the single sterogenic carbon centre, which is benzylic and further activated by the carboxylate, is readily racemised. However, in the case of methylphenidate, there are two stereogenic centres. While one centre is similarly benzylic and can be epimerised as indicated in U.S. Pat. No. 2,957,880, that converts the material into a mixture of two diastereoisomers and not into the racemate that is required for recycling.

SUMMARY OF THE INVENTION

This invention is based on the discovery of methods to effect racemisation of both chiral centres of methylphenidate. This process gives an optically inactive mixture of stereoisomers in which equilibrium may favour the threo isomer; the result is that undesired enantiomer is converted predominantly into the racemate of the threo isomer which can then be reintroduced into the resolution. The overall process of a combination of resolution and racemisation that may allow complete conversion in to the required isomer is outline in Scheme 1. The erythro isomer that may remain after the racemisation can be separated by conventional methods such as crystallisation at this stage and subjected further to the epimerisation conditions defined below. Alternatively, it can be recycled after passage through resolution of the threo isomer.

Scheme 1

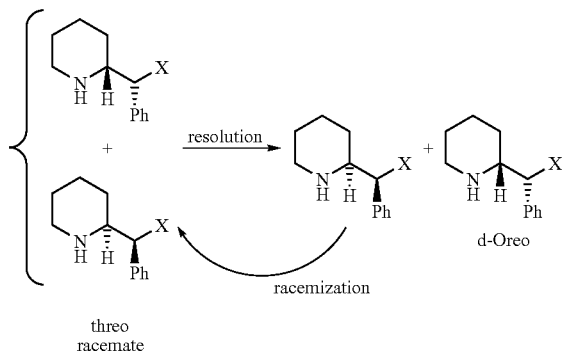

threo racemate

DESCRIPTION OF THE INVENTION

In Scheme 1, the group X may be the -CO$_2$Me function of methylphenidate. Resolution of this compound may be carried out by generally known procedures, e.g. by formation of a diastereoisomeric salt with a chiral acid. Alternatively, the resolution may be a biotransformation that modifies the group X in one enantiomer so that the enantiomers (of different compounds) are then readily separated.

This invention includes the means to effect racemisation at both stereogenic centres. It has been discovered that such racemisation can be carried out by way of activation at the piperidine nitrogen, which probably promotes a fragmentation of the ring, although the exact mechanism has not been ascertained. The putative olefinic intermediate has no chirality and recloses to a racemic mixture.

There are various ways in which the nitrogen maybe activated, to promote the elimination-addition mechanism. One approach is treatment with an acid, for example a carboxylic acid, at a sufficiently high temperature, such as heating with propionic acid, e.g. under reflux. This reaction is suitably conducted in an inert solvent such sa toluene. The racemisation can optionally be accelerated by the judicious addition of amounts of additives such as water or inorganic salts that will favour the charge separation in the transition state of the elimination. This reaction may also be promoted by the addition of an aldehyde or ketone (e.g. butyraldehyde or 2-cyclohexen-1-one).

As indicated above, conditions are known that will epimerise erythro-ritalinic acid at the benzylic centre only. On the basis of the evidence herein, it will readily be apparent to the man of ordinary skill in the art that conditions can be adopted, in order to give all 4 stereoisomers of methylphenidate, by racemisation at both chiral centres.

Following racemisation, and prior to resolution, it is necessary to enrich the mixture in the threo enantiomers. For example, the racemic methylphenidate is hydrolysed, e.g. using as such as alkali metal hydroxide. This can be done such that there is also epimerisation. Work-up with acid gives predominantly threo ritalinic acid (X=CO$_2$H), which can be esterified, e.g. by reaction with methanol, to give the appropriate substrate for resolution. Alternatively, the erythro isomers can be separated by precipitation, and then subjected to sequential epimerisation, esterification and resolution.

The following experiment was conducted in order to illustrate the feasibility of racemisation.

Propionic acid (2 ml) was added to a solution of d-threo-methylphenidate (5 g) in toluene (25 ml), and the solution was heated under reflux for 4 hours. The mixture was then cooled to ambient temperature, and was rinsed with dilute sodium carbonate and then with water. The organic phase was separated and dried with magnesium sulphate and evaporated under reduced pressure. The resulting oil (4.3 g) was analysed by chiral HPLC which indicated the presence of all 4 stereoisomers of methylphenidate in roughly equal proportions.

In order to preparing d-threo-methylphenidate by an efficient recycling process, the following protocol is adopted:

1) Resolve dl-threo-methylphenidate by the procedure described in the Example of PCT/GB97/00185 (International Publication No. WO 97/27176): Ditoluoyl-D-tartaric acid (5.033 g, 12.4 mmol) was suspended in a solution of 2% methanol in acetone (10 ml), and a solution of threo-methylphenidate (2.9 g, 12.4 mmol) in the same solvent (10 ml) was added. The solution was gently warmed to reflux whereupon all the reagents dissolved. The solution was immediately cooled and crystals began to form. The solution was allowed to stand at 4° C. for 17 hours and was then filtered. The crystals were washed with acetone (3×15 ml) and dried in vacuc to yield the ditoluoyl-D-tartrate salt of d-threo-methylphenidate (3.516 g, 44.3% by weight; corresponding to 97%. ee d-threo methylphenidate, as determined by chiral HPLC after salt cracking). The mother liquors were dried in vacuo to yield the ditoluoyl-D-tartrate salt of l-threo-methylphenidate as a solid, dry form (4.508 g, 50.5% yield, 88% ee).

The ditoluoyl-D-tartrate salt of d-threo-methylphenidate (3.486 g), obtained as described above, was suspended in 2% methanol in acetone, and warmed to c. 40° C. and cooled. This did not dissolve the solid which was stirred at room temperature for 24 hours. The suspension was filtered, the solid washed with acetone (10 ml) and dried in vacuo, to yield diastereomerically pure material (3.209 g, 92% recovery, corresponding to >99% ee d-threo-methylphenidate).

Repeating this protocol using isopropanol: methanol as the solvent, gave the same salt, on initial crystallization, enriched in at least 98%. Reslurrying increased this.

2) Racemise the residual l-threo-methylphenidate by the procedure described in the experiment above.
3) Hydrolyse the resultant racemic methylphenidate using 50% KOH and heating at reflux.
4) Esterify the resultant mixture of enantiomers, enriched in dl-threo-ritalinic acid, by reaction with MeOH and HCl.
5) Isolate the free base and recrystallise, to obtain essentially pure dl-threo-methylphenidate, suitable as a feedstock for resolution into constituent enantiomers.

We claim:

1. A process for obtaining single enantiomer d-threo-methylphenidate or l-threo-methylphenidate, which comprises resolution of a mixture of the d-threo-methylphenidate and l-threo-methylphenidate enantiomers; racemisation of the unwanted enantiomer, to give a mixture of all four stereoisomers, wherein the racemisation comprises reacting the unwanted enantiomer with an acid; enriching said mixture following racemisation wherein the d-threo and l-threo stereoisomers of methylphenidate are enriched over said d-erythro and l-erythro stereoisomers of methylphenidate; and separation of said d-erythro and l-erythro stereoisomers, to leave the said mixture of d-threo-methylphenidate and l-threo-methylphenidate enantiomers for resolution.

2. The process, according to claim 1, wherein the single enantiomer obtained is the d-threo isomer, i.e., the isomers of (R,R) absolute configuration.

3. The process, according to claim 1, wherein the racemisation comprises heating the unwanted enantiomer with an a chiral carboxylic acid.

4. The process, according to claim 1, wherein the separation is conducted following hydrolysis of the mixture of stereoisomers, to give ritalinic acid, and before or after re-esterification of the acid.

5. The process, according to claim 4, which additionally comprises equilibrating the product of hydrolysis wherein the threo diastereoisomer is preferentially obtained.

6. The process, according to claim 1, wherein the resolution is conducted using a chiral acid.

7. The process, according to claim 6, wherein the acid is O,O'-ditoluoyltartaric acid.

8. The process, according to claim 1, wherein the racemisation comprises heating the unwanted enantiomer with a carboxylic acid.

* * * * *

UNITED STATES PATENT AND TRADEMARK OFFICE
CERTIFICATE OF CORRECTION

PATENT NO. : 7,164,025 B2  Page 1 of 1
APPLICATION NO. : 09/928139
DATED : January 16, 2007
INVENTOR(S) : Marianne Langston and Hooshang Shahriari Zavareh It is certified that error appears in the above-identified patent and that said Letters Patent is hereby corrected as shown below:

Column 4,
Line 24 & 25 "enriched over said d-erythro" should read --enriched over the d-erythro--.
Line 33 & 34, "enantiomer with an a chiral carboxylic acid." should read --enantiomer with an achiral carboxylic acid.--.

Signed and Sealed this

Second Day of September, 2008

JON W. DUDAS
*Director of the United States Patent and Trademark Office*